United States Patent
Nagasaki et al.

(10) Patent No.: US 12,208,156 B2
(45) Date of Patent: Jan. 28, 2025

(54) CLEANSER

(71) Applicant: KAO CORPORATION, Tokyo (JP)

(72) Inventors: Yuko Nagasaki, Katsushika-ku (JP); Toshiaki Ozawa, Setagaya-ku (JP)

(73) Assignee: KAO CORPORATION, Tokyo (JP)

( * ) Notice: Subject to any disclaimer, the term of this patent is extended or adjusted under 35 U.S.C. 154(b) by 385 days.

(21) Appl. No.: 17/297,071

(22) PCT Filed: Nov. 27, 2019

(86) PCT No.: PCT/JP2019/046392
§ 371 (c)(1),
(2) Date: May 26, 2021

(87) PCT Pub. No.: WO2020/111131
PCT Pub. Date: Jun. 4, 2020

(65) Prior Publication Data
US 2022/0031599 A1    Feb. 3, 2022

(30) Foreign Application Priority Data

Nov. 27, 2018 (JP) .................................. 2018-221518

(51) Int. Cl.
| | | |
|---|---|---|
| *A61K 8/00* | (2006.01) | |
| *A61K 8/04* | (2006.01) | |
| *A61K 8/34* | (2006.01) | |
| *A61K 8/36* | (2006.01) | |
| *A61K 8/44* | (2006.01) | |
| *A61K 8/46* | (2006.01) | |
| *A61K 8/81* | (2006.01) | |
| *A61Q 19/10* | (2006.01) | |

(52) U.S. Cl.
CPC ............ *A61K 8/8152* (2013.01); *A61K 8/046* (2013.01); *A61K 8/345* (2013.01); *A61K 8/361* (2013.01); *A61K 8/442* (2013.01); *A61K 8/463* (2013.01); *A61K 8/466* (2013.01); *A61Q 19/10* (2013.01); *A61K 2800/87* (2013.01)

(58) Field of Classification Search
CPC .................................. C11D 8/152; C11D 8/056
See application file for complete search history.

(56) References Cited

U.S. PATENT DOCUMENTS

| | | | |
|---|---|---|---|
| 2008/0051314 A1* | 2/2008 | Wenzel | ............. A61Q 3/02 510/507 |
| 2009/0022818 A1 | 1/2009 | Sengupta et al. | |
| 2018/0311136 A1 | 11/2018 | Chang et al. | |

FOREIGN PATENT DOCUMENTS

| | | | |
|---|---|---|---|
| CN | 1929812 | A | 3/2007 |
| EP | 1 055 425 | A2 | 11/2000 |
| JP | 5-506259 | A | 9/1993 |
| JP | 2001-172668 | A | 6/2001 |
| JP | 2004-75791 | A | 3/2004 |
| JP | 2005-162666 | A | 6/2005 |
| JP | 2008-137904 | A | 6/2008 |
| JP | 2008-222641 | A | 9/2008 |
| JP | 2009-275009 | A | 11/2009 |
| JP | 2018-12650 | A | 1/2018 |
| JP | 2018-123342 | A | 8/2018 |

OTHER PUBLICATIONS

Extended European Search Report issued Oct. 7, 2022 in European Patent Application No. 19888939.6, 6 pages.
International Search Report issued on Dec. 24, 2019 in PCT/JP2019/046392 filed on Nov. 27, 2019, 3 pages.

* cited by examiner

*Primary Examiner* — Necholus Ogden, Jr.
(74) *Attorney, Agent, or Firm* — Oblon, McClelland, Maier & Neustadt, L.L.P.

(57) ABSTRACT

A cleanser including a non-aerosol foaming container and a liquid cleansing agent filled in the non-aerosol foaming container, the liquid cleansing agent containing the following components (A), (B) and (C): (A) an anionic surfactant, (B) from 0.1 to 2.5 mass % of a water-soluble polymer, wherein, in terms of the viscosity of a 1-mass % aqueous solution thereof, the ratio of viscosity v2 at a shear rate of $1.0 \times 10^{-2}$ $(s^{-1})$ to viscosity v1 at a shear rate of $1.0 \times 10^{-1}$ $(s^{-1})$ is $v2/v1 \geq 5$, and (C) water.

12 Claims, No Drawings

CLEANSER

FIELD OF THE INVENTION

The present invention relates to a cleanser.

BACKGROUND OF THE INVENTION

A liquid cleansing agent for skin or hair which is used by filling it in a foam dispensing container and dispensing it as a fine foam has the advantage of not only saving the trouble of foaming, but also of alleviating irritation to the skin, hair, and scalp because it produces a creamy foam. It is desired that the foam have elasticity and dense feeling when such a cleansing agent is dispensed from the container.

Generally, in a liquid cleansing composition, a thickener such as a water-soluble polymer is used in order to improve the quality of the foam after foaming.

For example, Patent Literature 1 discloses that a liquid cleansing agent containing an alkyl amino acid-based surfactant and a water-soluble polymer compound is low irritative and has good foaming properties when applied on the skin and hair. Such a proposal has also been made for a cleansing agent in a foaming container. Patent Literature 2 discloses that a liquid personal cleansing composition containing a surfactant and a viscosity-increasing polymer and packaged in a squeeze foamer is increased in viscosity due to the addition of a polymer, which enhances the quality of the foam (specifically, a creamy feeling of the foam).

However, in the case of a cleansing agent in a non-aerosol foaming container, it is necessary to make it easy to pass through a mesh upon dispensing the foam. Therefore, it is not preferable to increase the liquid viscosity of the cleansing agent in the container, and it is common to consider a formulation with a lower viscosity for dispensing a creamy and stable foam without clogging. For example, in Patent Literature 3, a liquid cleansing agent including cationized cellulose or a polyol instead of a thickener and having a low liquid viscosity is filled in a foam dispensing container.

(Patent Literature 1) JP-A-2001-172668
(Patent Literature 2) JP-A-H05-506259
(Patent Literature 3) JP-A-2005-162666

SUMMARY OF THE INVENTION

The present invention relates to a cleanser comprising:
a non-aerosol foaming container and,
a liquid cleansing agent filled in the non-aerosol foaming container, the liquid cleansing agent comprising the following components (A), (B) and (C):
(A) an anionic surfactant,
(B) from 0.1 to 2.5 mass % of a water-soluble polymer, wherein, in terms of the viscosity of a 1-mass % aqueous solution thereof, the ratio of viscosity $v2$ at a shear rate of $1.0 \times 10^{-2}$ $(s^{-1})$ to viscosity $v1$ at a shear rate of $1.0 \times 10^{-1}$ $(s^{-1})$ is $v2/v1 \geq 5$, and
(C) water.

DETAILED DESCRIPTION OF THE INVENTION

Regarding the cleansing agent of Patent Literature 3, the foam dispensed is a creamy but light one, and there is still room for improvement in terms of the dense feeling and elasticity of the foam felt upon spreading the foam with the palm of the hand. Meanwhile, where a thickener is used for a cleansing agent in a non-aerosol foaming container to improve the quality of the foam as in Patent Literature 1 and Patent Literature 2, even a small amount of thickener blended leads to an exponential increase of the liquid viscosity of the cleansing agent, and therefore to an increase in the pressure for pressing the foamer upon dispensing the foam, and this results in the inability to dispense or rather in the deterioration of the quality of the foam, which is a drawback.

The present inventors focused on the shear force acting on the cleansing agent upon dispensing from the foaming container, and conducted extensive studies. As a result, the present inventors found that it is possible to dispense an elastic and dense foam without increasing the pressure for pressing the container by combining a specific surfactant with a water-soluble polymer exhibiting specific viscosity characteristics and using it as a cleansing agent. In particular, the present inventors found that the dense feeling and elasticity of the foam dispensed from the foaming container are significantly improved without increasing the pressure for pressing the container when an anionic surfactant and a water-soluble polymer exhibiting specific viscosity characteristics are used in combination in a cleansing agent.

According to the cleanser of the present embodiment, it is possible to dispense an elastic and dense foam (elastic foam) from the non-aerosol foaming container without increasing the pressure for pressing the container.

In the cleanser of the present embodiment, a foaming surfactant is contained in a liquid cleansing agent to be filled in a non-aerosol foaming container. The foaming surfactant contains an anionic surfactant as component (A).

The anionic surfactant, component (A), is not limited as long as it is an anionic surfactant used in common cleansing agents, and examples thereof include carboxylic acid-based surfactants such as fatty acid salts and alkyl ether carboxylates; sulfate esters such as alkyl sulfates and alkyl ether sulfates; sulfonates such as sulfosuccinic acid alkyl ester salts, polyoxyalkylene sulfosuccinic acid alkyl ester salts, α-olefin sulfonates, and hydroxyalkane sulfonates; N-acyl amino acid salts, and N-acyl alkyl taurine salts.

Of these, in view of foaming and the quality of the foam, it is preferable to contain at least one selected from the group consisting of alkyl ether carboxylates, fatty acid salts, N-acyl amino acid salts, and alkyl ether sulfates. In particular, in view of improving the quality of the foam, it is preferable to contain a fatty acid salt. In view of improving detergency in addition to foaming and the quality of the foam, and of reducing irritation to the skin, it is preferable to contain an alkyl ether carboxylate, and it is more preferable to contain both a fatty acid salt and an alkyl ether carboxylate.

Examples of the alkyl ether carboxylate include those represented by formula (1).

$$R^1-O-(CH_2CH_2O)_n-CH_2-COOX \tag{1}$$

wherein, $R^1$ represents an alkyl group or an alkenyl group having from 8 to 20 carbon atoms; n represents the average number of moles of ethylene oxide added, and represents on average a number from 0.5 to 10; and X represents an alkali metal, an alkali earth metal, ammonium ($NH_4^+$), organic ammonium or a basic amino acid.

In formula (1), it is preferable that $R^1$ have from 10 to 18 carbon atoms, and more preferably from 12 to 16 carbon atoms, in view of improving detergency, foaming, and rinsability. From the same viewpoint, $R^1$ is preferably an alkyl group, and more preferably a linear alkyl group. From the same viewpoint, the average number of moles of ethylene oxide added n is preferably from 1 to 6.

Examples of X include alkali metals such as sodium and potassium; alkali earth metals such as calcium and magnesium; ammonium ($NH_4^+$); organic ammonium derived from alkanolamines such as monoethanolamine, diethanolamine and triethanolamine; and basic amino acids such as L-arginine. Among these, an alkali metal is preferable in view of improving foaming and rinsability.

As the fatty acid of the fatty acid salt, one having a linear or branched alkyl group or alkenyl group having from 9 to 21 carbon atoms is preferable. In view of improving foaming and rinsability, the number of carbon atoms in this group is preferably from 11 to 21, more preferably from 11 to 17, and even more preferably from 11 to 15. From the same viewpoint, this group is preferably an alkyl group, and more preferably a linear alkyl group.

Examples of the component which reacts with the fatty acid to produce a salt thereof include the same components as those described for X of the above-described alkyl ether carboxylate (1).

As the N-acyl amino acid salt, in view of foaming and the like, the acyl group is preferably derived from a fatty acid having a saturated or unsaturated linear or branched chain having from 8 to 18 carbon atoms, more preferably derived from a fatty acid having a saturated or unsaturated linear or branched chain having from 8 to 16 carbon atoms, and even more preferably derived from a fatty acid having a saturated or unsaturated linear or branched chain having from 8 to 14 carbon atoms. Examples of such fatty acids include caprylic acid, capric acid, lauric acid, myristic acid, palmitic acid, stearic acid, and oleic acid. Among these fatty acids, lauric acid, myristic acid, palmitic acid, and oleic acid are preferable, and lauric acid is more preferable, in view of the quality of the foam and storage stability. The acyl group of the N-acyl amino acid may be derived from a mixed fatty acid of the above-described fatty acids, and for example, may be obtained from coconut oil, palm kernel oil or the like as raw material. Among these, those obtained from coconut oil fatty acids or palm kernel fatty acids as raw material are preferable, and those obtained from coconut oil fatty acids as raw material are more preferable.

As the amino acid moiety of the N-acyl amino acid salt, a neutral amino acid selected from the group consisting of glycine and alanine, and an acidic amino acid selected from the group consisting of glutamic acid and aspartic acid are preferable, an acidic amino acid is more preferable, and glutamic acid is even more preferable, in view of the quality of the foam and good impression from use with a soft and moist skin after washing. These amino acid moieties may be any of D-form, L-form, or a mixture of D-form and L-form, and are preferably L-form.

In view of the quality of the foam and the like, the N-acyl amino acid is preferably N-lauroyl glutamic acid, N-myristoyl glutamic acid, N-cocoyl glutamic acid, N-palmoyl glutamic acid, N-lauroyl aspartic acid, N-cocoyl glycine, N-cocoyl alanine or a salt thereof, more preferably N-lauroyl glutamic acid, N-myristoyl glutamic acid, N-cocoyl glutamic acid, N-palmoyl glutamic acid, N-lauroyl aspartic acid, N-cocoyl glycine or a salt thereof, more preferably N-lauroyl glutamic acid, N-myristoyl glutamic acid, N-cocoyl glutamic acid, N-lauroyl aspartic acid or a salt thereof, even more preferably N-cocoyl glutamic acid, N-lauroyl aspartic acid or a salt thereof, and even more preferably N-cocoyl glutamic acid or a salt thereof.

In view of ensuring foaming and the quality of the foam, examples of the salt of the N-acyl amino acid salt include alkali metal salts such as sodium and potassium; alkali earth metal salts such as calcium and magnesium; other inorganic salts such as aluminum and zinc; ammonium salts; organic amine salts such as monoethanolamine, diethanolamine, triethanolamine, AMP (2-amino-2-methyl-1-propanol), and 2-amino-2-hydroxymethyl-1,3-propanediol; and other organic salts such as basic amino acid salts such as arginine, lysine, histidine, and ornithine. In view of skin irritation, alkali metal salts, triethanolamine salts and arginine salts are preferable, sodium salts, potassium salts, triethanolamine salts and arginine salts are more preferable, sodium salts and potassium salts are even more preferable, and sodium salts are even more preferable.

Examples of the alkyl ether sulfate include those represented by formula (2).

$$R^2—O—(CH_2CH_2O)_m—SO_3Y \qquad (2)$$

wherein, $R^2$ represents an alkyl group or an alkenyl group having from 8 to 22 carbon atoms; m is the average number of moles of ethylene oxide added, and represents a number from 0 to 20; and Y represents an alkali metal, an alkali earth metal, ammonium ($NH_4^+$), or organic ammonium.

In formula (2), $R^2$ is an alkyl group or an alkenyl group having from 8 to 22 carbon atoms, and may be either linear or branched. $R^2$ is preferably an alkyl group, more preferably having from 12 to 18 carbon atoms, and even more preferably having from 12 to 14 carbon atoms. m is more preferably from 0 to 12.

Examples of Y include the same as those described for X of the above-described alkyl ether carboxylate (1).

These compounds as the component (A) can be used singly or in combination of two or more thereof, and the content of the component (A) in the liquid cleansing agent is preferably 1 mass % or more, more preferably 3 mass % or more, and preferably 20 mass % or less, more preferably 10 mass % or less, in view of foaming, rinsability, and skin mildness. Moreover, the content of the component (A) in the liquid cleansing agent is preferably from 1 to 20 mass %, and more preferably from 3 to 10 mass %.

The water-soluble polymer, component (B), may be a thickener used in conventional cleansing agents, and in view of ensuring the quality of the foam after dispensing from the foamer, the viscosity v2 at a shear rate of $1.0\times10^{-2}$ ($s^{-1}$) may be 1 Pa·s or more in terms of the viscosity of a 1-mass % aqueous solution of the component (B).

In addition, the water-soluble polymer, component (B), has a ratio of viscosity v2 at a shear rate of $1.0\times10^{-1}$ ($s^{-1}$) to viscosity v1 at a shear rate of $1.0\times10^{-1}$ ($s^{-1}$) of v2/v1≥5, in terms of the viscosity of a 1-mass % aqueous solution thereof.

By using a water-soluble polymer having such viscosity characteristics in combination with a foaming surfactant, particularly the component (A), it is possible to suppress an increase in the pressure for pressing the foamer, even though the foam after dispensing from the foamer is dense and elastic, and it is also possible to achieve the good quality of the foam equal to that when the content of the component (A) is high, via the viscosity of the water remaining between the bubbles created by the foaming surfactant, even when the content of the component (A) is in a low concentration range which would normally result in poor quality of the foam.

Here, the viscosity is a value obtained by setting a 1-mass % aqueous solution of the component (B) in a rheometer, allowing it to stand for 5 minutes, and then measuring it at a shear rate from 0.0001 to 1,000 $s^{-1}$ with a measurement time from 30 to 2 s at 30° C.

More specifically, the viscosity is measured under the following conditions.

(Measuring Device)
MCR 502, Modular Compact Rheometer, Anton Paar
Measuring Cell: P-PTD200
Measuring System: CP75-1/Ti, d=0.041
(Measurement Conditions)

A 1-mass % aqueous solution of the component (B) is placed between plates, allowed to stand for 5 minutes, and then measured at a shear rate from 0.0001 to 1,000 s$^{-1}$ with a measurement time from 30 to 2 s at 30° C. In other words, when the viscosity is measured, the measurement time is varied according to the shear rate. For example, when the shear rate is 0.0001 s$^{-1}$, it is measured for a measurement time of 30 s, and when the shear rate is 1,000 s$^{-1}$, it is measured for a measurement time of 2 s.

It is also preferable that the water-soluble polymer, the component (B), have the above-mentioned viscosity ratio under a pH or degree of neutralization at which the water-soluble polymer suitably thickens, in view of improving the quality of the foam after dispensing from the foamer, and of suppressing the increase in the pressure for pressing the foaming container. When the polymer is a commercially available product, the conditions described in the catalog can be used as the conditions at which the water-soluble polymer suitably thickens. For example, when the component (B) is an anionic polymer, it is preferable to measure the above-mentioned viscosity ratio after neutralizing the polymer.

The above-mentioned viscosity v2 of the water-soluble polymer, component (B), is preferably 5 Pa·s or more, and more preferably 10 Pa·s or more, in view of ensuring the quality of the foam after dispensing from the foamer.

The above-mentioned viscosity ratio v2/v1 is preferably 6 or more, and more preferably 7 or more, in view of suppressing the increase in the pressure for pressing while retaining the dense feeling and elasticity of the foam dispensed from the foamer.

The component (B) may be any water-soluble polymer as long as it has the above-mentioned viscosity characteristics, but is preferably a polymer containing a repeating unit derived from acrylic acid and/or alkyl acrylate, and more preferably polyacrylic acid, cross-linked polyacrylic acid, acrylic acid copolymer, and cross-linked acrylic acid/alkyl acrylate copolymer, in view of foam dense feeling and elasticity. For example, one or more selected from the group consisting of carbomers, acrylates copolymers, and acrylates/C10-30 alkyl acrylate crosspolymers are preferable, and acrylates copolymers are more preferable.

Commercially available products of these water-soluble polymers can be used, such as Carbopol 910, Carbopol 934, Carbopol 940, Carbopol 941, Carbopol 980, Carbopol 981, Carbopol Ultrez 10, Carbopol Ultrez 30, and Carbopol ETD2050 (all manufactured by Lubrizol) as carbomers; Carbopol AQUA SF-1, and Carbopol AQUA SF-3 (all manufactured by Lubrizol) as acrylates copolymers; and Carbopol Ultrez 20, Carbopol Ultrez 21, and Carbopol ETD2020 (all manufactured by Lubrizol) as acrylates/C10-30 alkyl acrylate crosspolymers.

The compounds as the component (B) can be used singly or in combination of two or more thereof. In view of dispensing a foam having elasticity and a high dense feeling, the content of the component (B) in the liquid cleansing agent is 0.1 mass % or more, preferably 0.2 mass % or more, and more preferably 0.4 mass % or more. In view of suppressing an increase in the pressure for pressing the container, dispensing a foam having elasticity and a high dense feeling, and further improving the rinsability, the content of the component (B) is 2.5 mass % or less, preferably 2.3 mass % or less, and more preferably 2.0 mass % or less. In particular, in view of further improving the dense feeling and elasticity of the dispensed foam, the content of the component (B) is preferably 1.0 mass % or more, and in view of further improving the rinsability of the dispensed foam, the content of the component (B) is preferably 1.0 mass % or less.

The content of the component (B) in the liquid cleansing agent is from 0.1 to 2.5 mass %, preferably from 0.2 to 2.3 mass %, and more preferably from 0.4 to 2.0 mass %. In view of further improving the dense feeling and elasticity of the dispensed foam, the content of the component (B) is preferably from 1.0 to 2.0 mass %, and in view of further improving the rinsability of the dispensed foam, preferably from 0.4 to 1.0 mass %.

In the present embodiment, the mass ratio of the component (A) to the component (B), (A)/(B), is preferably 1 or more, more preferably 2 or more, even more preferably 3 or more, and even more preferably 4 or more, in view of foaming and dispensing a foam having a high dense feeling, and preferably 100 or less, more preferably 50 or less, even more preferably 30 or less, even more preferably 25 or less, and even more preferably 12 or less, in view of dispensing a foam having elasticity and a high dense feeling. The mass ratio of the component (A) to the component (B), (A)/(B), is preferably from 1 to 100, preferably from 2 to 50, more preferably from 3 to 30, even more preferably from 4 to 25, and even more preferably from 4 to 12.

In the present embodiment, the content of water, component (C), is the balance of the above components (A) and (B) and the other components contained as needed, and is preferably 40 mass % or more, more preferably 45 mass % or more, and preferably 90 mass % or less, more preferably 85 mass % or less in the liquid cleansing agent in view of satisfactorily dispersing or dissolving each component. The content of the component (C) in the liquid cleansing agent is preferably from 40 to 90 mass %, and more preferably from 45 to 85 mass %.

It is preferable that the liquid cleansing agent of the present embodiment further contain (D), a polyol, in view of further improving the dense feeling of the foam after dispensing from the foaming container by the synergistic effect with the components (A) and (B).

Examples of the polyol include ethylene glycol, diethylene glycol, hexylene glycol, polyethylene glycol, propylene glycol, dipropylene glycol, polypropylene glycol, isoprene glycol, 1,3-butylene glycol, glycerol, diglycerol, triglycerol, tetraglycerol, hexaglycerol, decaglycerol, and trimethyl propanol.

Of these, dihydric and trihydric alcohols are preferable, and propylene glycol and glycerol are more preferable, in view of foaming and dense feeling of the dispensed foam.

The polyols as the component (D) can be used singly or in combination of two or more thereof, and the content of the component (D) in the liquid cleansing agent is preferably 2 mass % or more, more preferably 5 mass % or more, and preferably 50 mass % or less, more preferably 40 mass % or less, in view of suppressing an increase in the pressure for pressing the container while maintaining the dense feeling of the foam. The content of the component (D) in the liquid cleansing agent is preferably from 2 to 50 mass %, and more preferably from 5 to 40 mass %.

The liquid cleansing agent of the present embodiment can further contain an amphoteric surfactant in view of foaming.

Examples of amphoteric surfactants include alkyl sulfobetaines, alkyl hydroxy sulfobetaines, alkyl carbobetaines, alkylamidehydroxysulfobetaines, alkylamideamine-type betaines, and alkylimidazoline-type betaines. Here, the number of carbon atoms of the alkyl group of the amphoteric surfactant is preferably from 8 to 20, and more preferably from 8 to 14.

Of these, the amphoteric surfactant is more preferably one or more selected from the group consisting of alkylamide propyl betaines and alkyl hydroxy sulfobetaines having an alkyl group having from 8 to 14 carbon atoms, even more preferably an alkyl hydroxy sulfobetaine, and even more preferably lauryl hydroxy sulfobetaine, in view of the quality of the foam and ease of rinsing.

The amphoteric surfactants can be used singly or in combination of two or more thereof, and the content of the amphoteric surfactant in the liquid cleansing agent is preferably 0.1 mass % or more, more preferably 0.5 mass % or more, and preferably 5 mass % or less, more preferably 4 mass % or less, in view of foaming and rinsability. The content of the amphoteric surfactant in the liquid cleansing agent is preferably from 0.1 to 5 mass %, and more preferably from 0.5 to 4 mass %.

In addition to the above components, the liquid cleansing agent of the present embodiment can contain components used in conventional cleansing agents as long as they do not undermine the effects of the present embodiment. Examples thereof include surfactants other than the above, lower alcohols such as ethanol and isopropyl alcohol, aromatic alcohols such as benzyl alcohol and benzyloxyethanol, cellosolves such as ethyl cellosolve and butyl cellosolve, carbitols such as ethyl carbitol and butyl carbitol, moisturizing ingredients such as sugars (derivatives), amino acids (derivatives), animal and plant (protein) derivatives, and animal and plant extracts, silicone derivatives such as polyoxyalkylene-modified silicones, inorganic or organic salts such as sodium sulfate, sodium carbonate, sodium hydrogen carbonate, potassium chloride, sodium chloride, and sodium citrate, pH adjusters such as acids and alkalis, anti-inflammatory agents such as glycyrrhetinic acid, glycyrrhizic acid and derivatives thereof, bactericides such as isopropyl methylphenol, preservatives, sequestering agents, antioxidants, ultraviolet absorbers, fragrances, vitamins, natural pigments such as chlorophyll and β-carotene, and colorants such as tar pigments.

The pH of the liquid cleansing agent of the present embodiment is preferably in the range from pH 5 to 11, and more preferably from pH 6 to 10, in view of ensuring a good impression from use and maintaining a low skin irritation potential.

In the present embodiment, the pH is obtained by measuring the stock solution of the liquid cleansing agent at 30° C. using a pH electrode.

The liquid cleansing agent of the present embodiment is in a liquid state, and its viscosity at 30° C. is preferably from 5 to 1,000 mPa·s, more preferably from 8 to 800 mPa·s, and even more preferably from 10 to 500 mPa·s, in view of suppressing an increase in the pressure for pressing the container while maintaining the dense feeling of the foam. In particular, in view of improving the rinsability, the viscosity is preferably 50 mPa·s or less, and more preferably 30 mPa·s or less. Also in particular, in view of dispensing denser and more elastic foam, the viscosity is preferably 30 mPa·s or more, and more preferably 50 mPa·s or more.

In the present embodiment, the viscosity of the liquid cleansing agent is measured at 30° C. using a Type-B viscometer (TVB-10 viscometer, manufactured by TOKI SANGYO CO., LTD.). Viscosities of less than 100 mPa·s are measured with Rotor No. 1 at a rotation speed of 60 rpm, viscosities from 100 to 199 mPa·s are measured with Rotor No. 1 at a rotation speed of 30 rpm, viscosities from 200 to 499 mPa·s are measured with Rotor No. 1 at a rotation speed of 12 rpm, and viscosities of 1,000 mPa·s or more are measured with Rotor No. 2 at a rotation speed of 12 rpm.

The liquid cleansing agent of the present embodiment is filled in a non-aerosol foaming container.

As the non-aerosol foaming container, any container can be used as long as it can mix the liquid cleansing agent with air and dispense it as a foam, and examples thereof include pump foamers which can dispense the content by being pressed at their pump head, and squeeze foamers which can dispense the content by being squeezed at the body thereof, specifically the foaming containers manufactured by Yoshino Kogyosho Co., Ltd. and Daiwa Can Company. In addition, for example, the foaming containers described in, for example, JP-A-H07-315463, JP-A-H08-230961, and JP-A-2005-193972 can also be used.

In particular, in view of convenience in environments in which a liquid cleansing agent is used, and of obtaining a dense and elastic foam, a pump foamer which can dispense the content by being pressed at the pump head is preferable, and in view of further improving the quality of the foam, a pump foamer equipped with a porous membrane filter in the dispensing passage is more preferable. As such a porous membrane filter, a filter from 90 to 400 mesh is preferable, a filter from 200 to 400 mesh is more preferable, and a filter from 200 to 305 mesh is even more preferable, in view of obtaining a good quality of the foam with a finer texture. It is preferable that one to three such porous filters be placed in the dispensing passage, and it is even more preferable that two such porous filters be placed.

The pump foamer has a complex drive mechanism and thus is easily affected by the pressing pressure. However, by using the liquid cleansing agent of the present embodiment, even a pump foamer can dispense a dense and highly elastic foam while suppressing the increase in the pressure for pressing.

Regarding the mixing ratio of the liquid cleansing agent and air in the pump foamer, for example, the dense feeling of the dispensed foam (mass of the liquid cleansing agent/volume of air) is preferably from 0.03 to 0.14 g/cm$^3$, and more preferably from 0.05 to 0.11 g/cm$^3$, in view of obtaining a sufficient volume of foam and the quality of the foam to easily wash the skin.

The liquid cleansing agent of the present embodiment is preferably used as a skin cleansing agent in a non-aerosol foaming container, and among the skin cleansing agents, it is preferably used as a hand soap, face wash, or body soap. The liquid cleansing agent of the present embodiment can be used to cleanse the skin by a common skin cleansing method. For example, the liquid cleansing agent can be used by pouring the foam dispensed from a non-aerosol foaming container onto one's hands, directly applying it to the skin without diluting it with water, making lather to cleanse, and then rinsing it using warm water from the shower or the like. It is also possible to pour the foam dispensed from the container onto one's hands and spread it directly by hand over the skin to wash.

Methods for cleansing the skin, other than the method of washing by hand, include washing with a sponge, towel, scrubbing brush, or the like made of cotton or synthetic fibers such as nylon. However, the method of directly pouring the foam onto one's hands and washing the skin by hand is preferable in view of reducing irritation to the skin and effectively achieving the foaming performance and impression from use.

With respect to the embodiments described above, the present description further discloses the following cleanser.

<1> A cleanser comprising:
a non-aerosol foaming container and, a liquid cleansing agent filled in the non-aerosol foaming container, the liquid cleansing agent comprising the following components (A), (B) and (C):
(A) an anionic surfactant,
(B) from 0.1 to 2.5 mass % of a water-soluble polymer, wherein, in terms of the viscosity of a 1-mass % aqueous solution thereof, the ratio of viscosity v2 at a shear rate of $1.0 \times 10^{-2}$ $(s^{-1})$ to viscosity v1 at a shear rate of $1.0 \times 10^{-1}$ $(s^{-1})$ is v2/v1≥5, and
(C) water.

<2> The cleanser according to <1>, wherein the component (A) preferably comprises at least one selected from the group consisting of alkyl ether carboxylates, fatty acid salts, N-acyl amino acid salts, and alkyl ether sulfates, more preferably a fatty acid salt, more preferably an alkyl ether carboxylate, and even more preferably both a fatty acid salt and an alkyl ether carboxylate.

<3> The cleanser according to <1> or <2>, wherein the component (A) preferably comprises an alkyl ether carboxylate represented by formula (1):

$$R^1-O-(CH_2CH_2O)_n-CH_2-COOX \quad (1)$$

wherein, $R^1$ represents an alkyl group or an alkenyl group having from 8 to 20 carbon atoms; n represents the average number of moles of ethylene oxide added, and represents on average a number from 0.5 to 10; and X represents an alkali metal, an alkali earth metal, ammonium ($NH_4^+$), organic ammonium or a basic amino acid.

<4> The cleanser according to <3>, wherein $R^1$ is a linear alkyl group having from 12 to 16 carbon atoms, n is from 1 to 6, and X is an alkali metal.

<5> The cleanser according to any one of <1> to <4>, wherein the component (A) comprises a fatty acid salt having a linear or branched alkyl group or alkenyl group having preferably from 9 to 21 carbon atoms, more preferably from 11 to 21 carbon atoms, even more preferably from 11 to 17 carbon atoms, and even more preferably from 11 to 15 carbon atoms.

<6> The cleanser according to <5>, wherein the fatty acid salt has a linear alkyl group having from 11 to 15 carbon atoms.

<7> The cleanser according to any one of <1> to <6>, wherein the component (A) is preferably at least one selected from the group consisting of N-lauroyl glutamic acid, N-myristoyl glutamic acid, N-cocoyl glutamic acid, N-palmoyl glutamic acid, N-lauroyl aspartic acid, N-cocoyl glycine, N-cocoyl alanine and the salts thereof, more preferably at least one selected from the group consisting of N-lauroyl glutamic acid, N-myristoyl glutamic acid, N-cocoyl glutamic acid, N-palmoyl glutamic acid, N-lauroyl aspartic acid, N-cocoyl glycine and the salts thereof, more preferably at least one selected from the group consisting of N-lauroyl glutamic acid, N-myristoyl glutamic acid, N-cocoyl glutamic acid, N-lauroyl aspartic acid and the salts thereof, even more preferably at least one selected from the group consisting of N-cocoyl glutamic acid, N-lauroyl aspartic acid and the salts thereof, and even more preferably N-cocoyl glutamic acid or a salt thereof.

<8> The cleanser according to any one of <1> to <7>, wherein the water-soluble polymer, component (B), is preferably a polymer comprising a repeating unit derived from acrylic acid and/or alkyl acrylate, more preferably one or more selected from the group consisting of polyacrylic acid, cross-linked polyacrylic acid, acrylic acid copolymer, and cross-linked acrylic acid/alkyl acrylate copolymer, even more preferably one or more selected from the group consisting of carbomers, acrylates copolymers, and acrylates/C10-30 alkyl acrylate crosspolymers, and even more preferably an acrylates copolymer.

<9> The cleanser according to any one of <1> to <8>, wherein preferably:
the component (A) comprises both a fatty acid salt and an alkyl ether carboxylate; and
the component (B) is one or more selected from the group consisting of carbomers, acrylates copolymers, and acrylates/C10-30 alkyl acrylate crosspolymers.

<10> The cleanser according to any one of <1> to <9>, wherein the component (A) preferably comprises a fatty acid salt having a linear alkyl group having from 11 to 15 carbon atoms, and an alkyl ether carboxylate represented by formula (1):

$$R^1-O-(CH_2CH_2O)_n-CH_2-COOX \quad (1)$$

wherein, $R^1$ represents a linear alkyl group having from 12 to 16 carbon atoms; n represents the average number of moles of ethylene oxide added, and represents on average a number from 1 to 6; and X represents an alkali metal.

<11> The cleanser according to any one of <1> to <10>, wherein the content of the component (A) in the liquid cleansing agent is preferably 1 mass % or more, more preferably 3 mass % or more, and preferably 20 mass % or less, more preferably 10 mass % or less.

<12> The cleanser according to any one of <1> to <11>, wherein the content of the component (B) in the liquid cleansing agent is preferably 0.2 mass % or more, more preferably 0.4 mass % or more, and preferably 2.3 mass % or less, more preferably 2.0 mass % or less.

<13> The cleanser according to any one of <1> to <12>, wherein the content of the component (B) in the liquid cleansing agent is preferably 1.0 mass % or more.

<14> The cleanser according to any one of <1> to <12>, wherein the content of the component (B) in the liquid cleansing agent is preferably 1.0 mass % or less.

<15> The cleanser according to any one of <1> to <14>, wherein, preferably, the content of the component (A) is 3 mass % or more, and the content of the component (B) is 0.4 mass % or more in the liquid cleansing agent.

<16> The cleanser according to any one of <1> to <14>, wherein, preferably, the content of the component (A) is 3 mass % or more, and the content of the component (B) is 2.0 mass % or less in the liquid cleansing agent.

<17> The cleanser according to any one of <1> to <14>, wherein, preferably, the content of the component (A) is 10 mass % or less, and the content of the component (B) is 0.4 mass % or more in the liquid cleansing agent.

<18> The cleanser according to any one of <1> to <14>, wherein, preferably, the content of the component (A) is 10 mass % or less, and the content of the component (B) is 2.0 mass % or less in the liquid cleansing agent.

<19> The cleanser according to any one of <1> to <18>, wherein the mass ratio of the component (A) to the component (B), (A)/(B), is preferably 1 or more, more preferably 2 or more, even more preferably 3 or more, and even more preferably 4 or more, and preferably 100 or less, more preferably 50 or less, even more preferably 30 or less, even more preferably 25 or less, and even more preferably 12 or less.

<20> The cleanser according to any one of <1> to <19>, wherein the viscosity v2 at a shear rate of $1.0 \times 10^{-2}$ ($s^{-1}$) is preferably 1 Pa·s or more, more preferably 5 Pa·s or more, and even more preferably 10 Pa·s or more, in terms of the viscosity of a 1-mass % aqueous solution of the component (B).

<21> The cleanser according to any one of <1> to <20>, wherein the water-soluble polymer, component (B), has a ratio of viscosity v2 at a shear rate of $1.0 \times 10^{-2}$ ($s^{-1}$) to viscosity v1 at a shear rate of $1.0 \times 10^{-1}$ ($s^{-1}$) of preferably 6 or more, and more preferably 7 or more, in terms of the viscosity of a 1-mass % aqueous solution thereof.

<22> The cleanser according to any one of <1> to <21>, wherein the water-soluble polymer, component (B), is an anionic polymer, and when the polymer is neutralized, the ratio of viscosity v2 at a shear rate of $1.0 \times 10^{-2}$ ($s^{-1}$) to viscosity v1 at a shear rate of $1.0 \times 10^{-1}$ ($s^{-1}$), (v2/v1), is 5 or more, more preferably 6 or more, and even more preferably 7 or more, in terms of the viscosity of a 1-mass % aqueous solution thereof.

<23> The cleanser according to any one of <1> to <22>, wherein the liquid cleansing agent preferably further comprise (D), a polyol.

<24> The cleanser according to <23>, wherein the polyol, component (D), is preferably a dihydric or trihydric alcohol, and more preferably propylene glycol or glycerol.

<25> The cleanser according to <23> or <24>, wherein the content of the component (D) in the liquid cleansing agent is preferably 2 mass % or more, more preferably 5 mass % or more, and preferably 50 mass % or less, more preferably 40 mass % or less.

<26> The cleanser according to any one of <1> to <25>, wherein the liquid cleansing agent preferably further comprise an amphoteric surfactant.

<27> The cleanser according to any one of <1> to <26>, wherein the pH of the liquid cleansing agent is preferably from 5 to 11, and more preferably from 6 to 10.

<28> The cleanser according to any one of <1> to <27>, wherein the viscosity at 30° C. of the liquid cleansing agent is preferably from 5 to 1,000 mPa·s, more preferably from 8 to 800 mPa·s, and even more preferably from 10 to 500 mPa·s.

<29> The cleanser according to any one of <1> to <28>, wherein the viscosity at 30° C. of the liquid cleansing agent is preferably 50 mPa·s or less, and more preferably 30 mPa·s or less.

<30> The cleanser according to any one of <1> to <29>, wherein the viscosity at 30° C. of the liquid cleansing agent is preferably 30 mPa·s or more, and more preferably 50 mPa·s or more.

<31> The cleanser according to any one of <1> to <30>, wherein the non-aerosol foaming container is preferably a pump foamer or a squeeze foamer, and more preferably a pump foamer.

<32> The cleanser according to any one of <1> to <30>, wherein the non-aerosol foaming container is preferably a pump foamer, the pump foamer is more preferably equipped with a filter from 90 to 400 mesh in the dispensing passage, and the filter is even more preferably a porous membrane.

<33> The cleanser according to any one of <1> to <32>, wherein the liquid cleansing agent is preferably for cleansing the skin, and more preferably used as a hand soap, face wash, or body soap.

<34> A cleanser comprising:
a non-aerosol foaming container and,
a liquid cleansing agent filled in the non-aerosol foaming container, the liquid cleansing agent comprising the following components (A), (B) and (C):
(A) from 3 to 10 mass % of an anionic surfactant,
(B) from 0.1 to 2.5 mass % of a water-soluble polymer, wherein, in terms of the viscosity of a 1-mass % aqueous solution thereof, the ratio of viscosity v2 at a shear rate of $1.0 \times 10^{-2}$ ($s^{-1}$) to viscosity v1 at a shear rate of $1.0 \times 10^{-1}$ ($s^{-1}$) is v2/v1≥5, and
(C) water
and having a viscosity at 30° C. of 30 mPa·s or more.

<35> A cleanser comprising:
a non-aerosol foaming container and,
a liquid cleansing agent filled in the non-aerosol foaming container, the liquid cleansing agent comprising the following components (A), (B) and (C):
(A) from 3 to 10 mass % of an anionic surfactant,
(B) from 0.1 to 2.5 mass % of a water-soluble polymer, wherein, in terms of the viscosity of a 1-mass % aqueous solution thereof, the ratio of viscosity v2 at a shear rate of $1.0 \times 10^{-2}$ ($s^{-1}$) to viscosity v1 at a shear rate of $1.0 \times 10^{-1}$ ($s^{-1}$) is v2/v1≥5, and
(C) water
and having a viscosity at 30° C. of 50 mPa·s or less.

<36> The cleanser according to <34> or <35>, wherein the viscosity v2 at a shear rate of $1.0 \times 10^{-2}$ ($s^{-1}$) of a 1-mass % aqueous solution of the component (B) is preferably 1 Pa·s or more, more preferably 5 Pa·s or more, and even more preferably 10 Pa·s or more.

<37> A liquid cleansing composition in a non-aerosol foaming container, comprising the following components (A), (B) and (C):
(A) from 1 to 20 mass % of an anionic surfactant selected from the group consisting of alkyl ether carboxylates and fatty acid salts,
(B) from 0.1 to 2.5 mass % of a water-soluble polymer selected from the group consisting of polyacrylic acid, cross-linked polyacrylic acid, acrylic acid copolymer, and cross-linked acrylic acid/alkyl acrylate copolymer, wherein, in terms of the viscosity of a 1-mass % aqueous solution thereof, the ratio of viscosity v2 at a shear rate of $1.0 \times 10^{-2}$ ($s^{-1}$) to viscosity v1 at a shear rate of $1.0 \times 10^{-1}$ ($s^{-1}$) is v2/v1≥5,
(C) water
and filled in a container equipped with a filter from 90 to 400 mesh.

<38> A cleanser comprising:
a non-aerosol foaming container equipped with a filter from 90 to 400 mesh and,
a liquid cleansing agent filled in the non-aerosol foaming container, the liquid cleansing agent comprising the following components (A), (B) and (C):
(A) an anionic surfactant,
(B) from 0.1 to 2.5 mass % of one or more water-soluble polymers selected from the group consisting of polyacrylic acid, cross-linked polyacrylic acid, acrylic acid copolymer, and cross-linked acrylic acid/alkyl acrylate copolymer, wherein, in terms of the viscosity of a 1-mass % aqueous solution thereof, the ratio of viscosity v2 at a shear rate of $1.0 \times 10^{-2}$ ($s^{-2}$) to viscosity v1 at a shear rate of $1.0 \times 10^{-2}$ ($s^{-2}$) is v2/v1≥5, and (C) water and having a viscosity at 30° C. from 5 to 1,000 mPa·s.

<39> A cleansing method comprising
dispensing a foam of a liquid cleansing agent in a non-aerosol foaming container from the container, wherein the liquid cleansing agent comprises the following components (A), (B) and (C):
(A) an anionic surfactant,
(B) from 0.1 to 2.5 mass % of a water-soluble polymer, wherein, in terms of the viscosity of a 1-mass % aqueous solution thereof, the ratio of viscosity v2 at a shear rate of $1.0 \times 10^{-2}$ $(s^{-1})$ to viscosity v1 at a shear rate of $1.0 \times 10^{-1}$ $(s^{-2})$ is v2/v1≥5,
(C) water; and
spreading the foam over the skin to wash the skin.

<40> The cleansing method according to <39>, wherein the foam is poured onto one's hands, and spread directly by hand over the skin to wash the skin.

<41> Use of a liquid cleansing agent as a skin cleansing agent in a non-aerosol foaming container, the liquid cleansing agent comprising the following components (A), (B) and (C):
(A) an anionic surfactant,
(B) from 0.1 to 2.5 mass % of a water-soluble polymer, wherein, in terms of the viscosity of a 1-mass % aqueous solution thereof, the ratio of viscosity v2 at a shear rate of $1.0 \times 10^{-2}$ $(s^{-1})$ to viscosity v1 at a shear rate of $1.0 \times 10^{-1}$ $(s^{-1})$ is v2/v1≥5,
(C) water.

<42> Use of the liquid cleansing agent for producing a cleanser by filling the liquid cleansing agent in a non-aerosol foaming container, the liquid cleansing agent comprising the following components (A), (B) and (C):
(A) an anionic surfactant,
(B) from 0.1 to 2.5 mass % of a water-soluble polymer, wherein, in terms of the viscosity of a 1-mass % aqueous solution thereof, the ratio of viscosity v2 at a shear rate of $1.0 \times 10^{-2}$ $(s^{-1})$ to viscosity v1 at a shear rate of $1.0 \times 10^{-1}$ $(s^{-1})$ is v2/v1≥5,
(C) water.

<43> A method for producing a foam, comprising filling a liquid composition in a non-aerosol foaming container, wherein the liquid composition comprises:
a foaming surfactant,
from 0.1 to 2.5 mass % of a water-soluble polymer, wherein, in terms of the viscosity of a 1-mass % aqueous solution thereof, the ratio of viscosity v2 at a shear rate of $1.0 \times 10^{-2}$ $(s^{-1})$ to viscosity v1 at a shear rate of $1.0 \times 10^{-1}$ $(5^{-1})$ is v2/v1≥5, and
water; and
dispensing a foam of the liquid composition by pressing the container.

EXAMPLES

Examples 1 to 16 and Comparative Examples 1 to 7

For each water-soluble polymer shown in Table 1, a 1-mass % aqueous solution was prepared, and the viscosity v1 at a shear rate of $1.0 \times 10^{-1}$ $(s^{-1})$ and the viscosity v2 at a shear rate of $1.0 \times 10^{-2}$ $(s^{-1})$ were measured under neutralizing conditions according to the method described above to determine the ratio [v2/v1]. The results are shown in Table 1.

Liquid cleansing agents having compositions shown in Tables 2 and 3 were produced by mixing and dissolving the components in water. The resulting liquid cleansing agents were filled in a pump foamer (160 mL [YF-9413, manufactured by Yoshino Kogyosho Co., Ltd.], a type of container in which contents pass through two filers, specifically, a lower filter of 200 mesh and an upper filter of 305 mesh) to obtain the cleansers. The viscosity and pH of the liquid cleansing agents before filling were measured, and the ease of pressing the pump, the pressure for pressing the pump, the elasticity of the foam upon dispensing, the dense feeling of the foam, and the quickness of rinsing were evaluated. The results are shown in both Tables 2 and 3.

(Evaluation Method)

(1) Viscosity:

For each liquid cleansing agent, the viscosity was measured at 30° C. for a measurement time of 1 minute using a Type-B viscometer (TVB-10 viscometer, manufactured by TOKI SANGYO CO., LTD.).

Viscosities of less than 100 mPa·s were measured with Rotor No. 1 at a rotation speed of 60 rpm, viscosities from 100 to 199 mPa·s were measured with Rotor No. 1 at a rotation speed of 30 rpm, viscosities from 200 to 499 mPa·s were measured with Rotor No. 1 at a rotation speed of 12 rpm, and viscosities of 1,000 mPa-s or more were measured with Rotor No. 2 at a rotation speed of 12 rpm.

(2) pH:

The pH of the stock solution of each liquid cleansing agent was measured at 30° C. using a pH electrode.

(3) Ease of Pressing the Pump:

Three professional panelists evaluated the ease of pressing the pump when pressing the pump with the palm of the hand to dispense foam from the outlet in accordance with the following criteria.

The evaluation results determined by discussion based on the evaluations by the three professional panelists are shown.

5: Very easy to press.
4: Easy to press.
3: Slightly easy to press.
2: Slightly heavy and difficult to press.
1: Very heavy and difficult to press.

(4) Pressure for Pressing the Pump:

Using a tester for the pressure for pressing, the pump head was pressed in a vertical direction at a constant speed of 50 mm/s, and the load applied to the sensor in contact with the pump head at that time was measured. More specifically, the pump foamer was placed in the tester for the pressure for pressing so that the pump head came into contact with the sensor part of the tester for the pressure for pressing, and the load when pressing the pump head to the bottom end was measured.

(5) Elasticity of the Foam Upon Dispensing:

Three professional panelists dispensed foam (liquid volume: 2 mL) from the outlet of the container onto one palm of the hand wet with water, and then immediately pressed the dispensed foam with the other hand from above to evaluate the degree of elasticity of the foam felt by the other hand in accordance with the following criteria.

The evaluation results determined by discussion based on the evaluations by the three professional panelists are shown.

5: Very elastic.
4: Elastic.
3: Slightly elastic.
2: Slightly not elastic.
1: Not elastic.

(6) Dense Feeling of Foam:

Three professional panelists dispensed foam (liquid volume: 2 mL) from the outlet of the container onto one palm of the hand wet with water, and then immediately held the dispensed foam between both hands and rubbed them together 20 times back and forth to evaluate the degree of dense feeling of the foam felt by the hands in accordance with the following criteria.

The evaluation results determined by discussion based on the evaluations by the three professional panelists are shown.
- 5: Very dense.
- 4: Dense.
- 3: Slightly dense.
- 2: Slightly not dense.
- 1: Not dense.

(7) Quickness of Rinsing:

Three professional panelists dispensed foam (liquid volume: 2 mL) onto one forearm wet with water, then immediately rubbed it 20 times back and forth with the other hand, and then repeatedly poured 10 mL of tap water in a plastic container until the panelist did no longer feel slimy on the forearm when touching with the other hand, to count the number of times of pouring tap water. The results are shown in accordance with the following criteria.
- a: 3 times or less.
- b: 4 or 5 times.
- d: 6 times or more.

TABLE 1

| Component | Product Name | v2/v1 |
|---|---|---|
| Acrylates Copolymer | Carbopol AQUA SF-1 | 8.7 |
|  | Carbopol AQUA SF-3 | 8.1 |
| Carbomer | Carbopol 981 | 5.4 |
|  | Carbopol ETD 2050 | 6.7 |
| Acrylates/C10-30 Alkyl Acrylate Cosspolymer | Carbopol ETD 2020 | 5.7 |
|  | Carbopol Ultrez 20 | 5.8 |
|  | PEMULEN TR-2 POLYMERIC EMULSIFIER | 3.0 |
| Hydroxyethyl Cellulose | HEC SE850K | 1.3 |
| Hydroxypropyl Cellulose | HPC M | 1.8 |
| Hydroxypropyl Guar Hydroxypropyltrimonium Chloride | Jaguar C-162 | 1.2 |

TABLE 2

| Component (mass %) |  | Example 1 | Example 2 | Example 3 | Example 4 | Example 5 | Example 6 |
|---|---|---|---|---|---|---|---|
| (A) Laureth-6 Carboxylic acid | AKYPO RLM-45 CA | 1.8 | 1.8 | 1.8 | 1.8 | 1.8 | 0.36 |
| Laureth-4 Carboxylic acid | AKYPO LM-26C | 0.09 | 0.09 | 0.09 | 0.09 | 0.09 | 0.018 |
| Lauric Acid | Lunac L-98 | 3.8 | 3.8 | 3.8 | 3.8 | 3.8 | 0.76 |
| Myristic Acid | Lunac MY-98 | 0.85 | 0.85 | 0.85 | 0.85 | 0.85 | 0.17 |
| Palmitic Acid | Lunac P-95 | 0.26 | 0.26 | 0.26 | 0.26 | 0.26 | 0.052 |
| Sodium Cocoyl Glutamate | AMISOFT CS-22B |  |  |  |  |  |  |
| Sodium Polyoxyethylene Lauryl Sulfate | Emal 227-PH11K2 |  |  |  |  |  |  |
| Lauryl Hydroxysultaine | AMPHITOL 20HD | 0.92 | 0.92 | 0.92 | 0.92 | 0.92 | 0.184 |
| Potassium Hydroxide |  | 1.58 | 1.64 | 1.82 | 1.85 | 1.82 | 0.43 |
| (D) Propylene Glycol |  | 10 | 10 | 10 | 10 |  | 10 |
| Acrylates Copolymer | Carbopol AQUA SF-1 POLYMER | 0.2 | 0.5 | 1.27 | 1.5 | 1.27 | 0.6 |
| (B) Carbomer | Carbopol 981 |  |  |  |  |  |  |
| Carbomer | Carbopol ETD 2050 |  |  |  |  |  |  |
| Acrylates/C10-30 Alkyl Acrylate Crosspolymer | Carbopol ETD 2020 |  |  |  |  |  |  |
| Acrylates/C10-30 Alkyl Acrylate Crosspolymer | Carbopol Ultrez 20 |  |  |  |  |  |  |
| Acrylates/C10-30 Alkyl Acrylate Crosspolymer | PEMULEN TR-2 POLYMERIC EMULSIFIER |  |  |  |  |  |  |
| Acrylates Copolymer | Carbopol AQUA SF-3 POLYMER |  |  |  |  |  |  |
| Hydroxyethyl Cellulose | HEC Daicel SE850K |  |  |  |  |  |  |
| Hydroxypropyl Cellulose | HPC M |  |  |  |  |  |  |
| Hydroxypropyl Guar Hydroxypropyltrimonium Chloride | Jaguar C-162 |  |  |  |  |  |  |
| (C) Purified Water |  | Balance | Balance | Balance | Balance | Balance | Balance |
| Total |  | 100 | 100 | 100 | 100 | 100 | 100 |
| (A) Total |  | 6.8 | 6.8 | 6.8 | 6.8 | 6.8 | 1.36 |
| (B) Total |  | 0.2 | 0.5 | 1.27 | 1.5 | 1.27 | 0.6 |
| (A)/(B) |  | 34 | 13.6 | 5.35 | 4.53 | 5.35 | 2.27 |
| Viscosity (Type-B Viscometer, 30° C.) [mPa · s] |  | 6.2 | 8.8 | 71.4 | 177.1 | 95 | 51 |
| pH (30° C., Stock Solution) |  | 9.2 | 9.2 | 9.0 | 8.9 | 9.4 | 8.8 |
| Ease of Pressing Pump |  | 5 | 5 | 4 | 4 | 4 | 5 |
| Pressure for Pressing Pump (50 mm/s) [N] |  | 29 | 32 | 34 | 35 | 34 | 33 |
| Elasticity of Foam upon Dispensing |  | 3 | 4 | 5 | 5 | 5 | 5 |
| Dense feeling of Foam |  | 3 | 4 | 5 | 5 | 4 | 4 |
| Quickness of Rinsing |  | a | a | b | b | b | a |

TABLE 2-continued

| Component (mass %) | | Example 7 | Example 8 | Example 9 | Example 10 | Example 11 |
|---|---|---|---|---|---|---|
| (A) Laureth-6 Carboxylic acid | AKYPO RLM-45 CA | 0.36 | 3.6 | | | |
| Laureth-4 Carboxylic acid | AKYPO LM-26C | 0.018 | 0.18 | | | |
| Lauric Acid | Lunac L-98 | 0.76 | 7.6 | 8 | | |
| Myristic Acid | Lunac MY-98 | 0.17 | 1.7 | | | |
| Palmitic Acid | Lunac P-95 | 0.052 | 0.52 | | | |
| Sodium Cocoyl Glutamate | AMISOFT CS-22B | | | | 8 | |
| Sodium Polyoxyethylene Lauryl Sulfate | Emal 227-PH11K2 | | | | | 8 |
| Lauryl Hydroxysultaine | AMPHITOL 20HD | 0.184 | 1.84 | | | |
| Potassium Hydroxide | | 0.60 | 3.36 | 2.43 | 0.22 | 0.22 |
| (D) Propylene Glycol | | 10 | 10 | 10 | 10 | 10 |
| Acrylates Copolymer | Carbopol AQUA SF-1 POLYMER | 1.27 | 1.27 | 1.32 | 1.5 | 1.5 |
| (B) Carbomer | Carbopol 981 | | | | | |
| Carbomer | Carbopol ETD 2050 | | | | | |
| Acrylates/C10-30 Alkyl Acrylate Crosspolymer | Carbopol ETD 2020 | | | | | |
| Acrylates/C10-30 Alkyl Acrylate Crosspolymer | Carbopol Ultrez 20 | | | | | |
| Acrylates/C10-30 Alkyl Acrylate Crosspolymer | PEMULEN TR-2 POLYMERIC EMULSIFIER | | | | | |
| Acrylates Copolymer | Carbopol AQUA SF-3 POLYMER | | | | | |
| Hydroxyethyl Cellulose | HEC Daicel SE850K | | | | | |
| Hydroxypropyl Cellulose | HPC M | | | | | |
| Hydroxypropyl Guar Hydroxypropyltrimonium Chloride | Jaguar C-162 | | | | | |
| (C) Purified Water | | Balance | Balance | Balance | Balance | Balance |
| Total | | 100 | 100 | 100 | 100 | 100 |
| (A) Total | | 1.36 | 13.6 | 8 | 8 | 8 |
| (B) Total | | 1.27 | 1.27 | 1.32 | 1.5 | 1.5 |
| (A)/(B) | | 1.07 | 10.7 | 6.06 | 5.33 | 5.33 |
| Viscosity (Type-B Viscometer, 30° C.) [mPa · s] | | 416.8 | 74.3 | 150.1 | 189 | 370.6 |
| pH (30° C., Stock Solution) | | 9.7 | 9.0 | 9.3 | 6.7 | 6.7 |
| Ease of Pressing Pump | | 4 | 4 | 4 | 4 | 4 |
| Pressure for Pressing Pump (50 mm/s) [N] | | 35 | 37 | 34 | 35 | 35 |
| Elasticity of Foam upon Dispensing | | 5 | 5 | 4 | 5 | 4 |
| Dense feeling of Foam | | 5 | 5 | 4 | 5 | 4 |
| Quickness of Rinsing | | b | b | b | b | b |

TABLE 3

| Component (mass %) | | Example 12 | Example 13 | Example 14 | Example 15 | Example 16 | Comparative Example 1 |
|---|---|---|---|---|---|---|---|
| (A) Laureth-6 Carboxylic acid | AKYPO RLM-45 CA | 1.8 | 1.8 | 1.8 | 1.8 | 1.8 | 1.8 |
| Laureth-4 Carboxylic acid | AKYPO LM-26C | 0.09 | 0.09 | 0.09 | 0.09 | 0.09 | 0.09 |
| Lauric Acid | Lunac L-98 | 3.8 | 3.8 | 3.8 | 3.8 | 3.8 | 3.8 |
| Myristic Acid | Lunac MY-98 | 0.85 | 0.85 | 0.85 | 0.85 | 0.85 | 0.85 |
| Palmitic Acid | Lunac P-95 | 0.26 | 0.26 | 0.26 | 0.26 | 0.26 | 0.26 |
| Sodium Cocoyl Glutamate | AMISOFT CS-22B | | | | | | |
| Sodium Polyoxyethylene Lauryl Sulfate | Emal 227-PH11K2 | | | | | | |
| Lauryl Hydroxysultaine | AMPHITOL 20HD | 0.92 | 0.92 | 0.92 | 0.92 | 0.92 | 0.92 |
| Potassium Hydroxide | | 1.92 | 1.87 | 1.70 | 1.70 | 1.85 | 1.54 |
| (D) Propylene Glycol | | 10 | 10 | 10 | 10 | 10 | 10 |
| (B) Acrylates Copolymer | Carbopol AQUA SF-1 POLYMER | | | | | | |
| Carbomer | Carbopol 981 | 0.5 | | | | | |
| Carbomer | Carbopol ETD 2050 | | 0.5 | | | | |
| Acrylates/C10-30 Alkyl Acrylate Crosspolymer | Carbopol ETD 2020 | | | 0.25 | | | |
| Acrylates/C10-30 Alkyl Acrylate Crosspolymer | Carbopol Ultrez 20 | | | | 0.25 | | |
| Acrylates/C10-30 Alkyl Acrylate Crosspolymer | PEMULEN TR-2 POLYMERIC EMULSIFIER | | | | | | |
| Acrylates Copolymer | Carbopol AQUA SF-3 POLYMER | | | | | 1.5 | |

TABLE 3-continued

|  |  |  |  |  |  |  |  |
|---|---|---|---|---|---|---|---|
| Hydroxyethyl Cellulose | HEC Daicel SE850K |  |  |  |  |  |  |
| Hydroxypropyl Cellulose | HPC M |  |  |  |  |  |  |
| Hydroxypropyl Guar | Jaguar C-162 |  |  |  |  |  |  |
| Hydroxypropyltrimonium Chloride |  |  |  |  |  |  |  |
| (C) Purified Water |  | Balance | Balance | Balance | Balance | Balance | Balance |
|  | Total | 100 | 100 | 100 | 100 | 100 | 100 |
|  | (A) Total | 6.8 | 6.8 | 6.8 | 6.8 | 6.8 | 6.8 |
|  | (B) Total | 0.5 | 0.5 | 0.25 | 0.25 | 1.5 | 0 |
|  | (A)/(B) | 13.6 | 13.6 | 27.2 | 27.2 | 4.53 | — |
|  | Viscosity (Type-B Viscometer, 30° C.) [mPa · s] | 63.5 | 51.7 | 13.6 | 17.9 | 87.1 | 4.9 |
|  | pH (30° C., Stock Solution) | 9.1 | 8.9 | 9.2 | 9.2 | 8.3 | 9.0 |
|  | Ease of Pressing Pump | 3 | 3 | 4 | 4 | 4 | 5 |
|  | Pressure upon Pressing Pump (50 mm/s) [N] | 41 | 39 | 34 | 34 | 33 | 31 |
|  | Elasticity of Foam upon Dispensing | 3 | 3 | 4 | 4 | 5 | 1 |
|  | Dense feeling of Foam | 4 | 4 | 4 | 4 | 5 | 1 |
|  | Quickness of Rinsing | b | b | b | b | b | a |

|  |  | Comparative Example |  |  |  |  |  |
|---|---|---|---|---|---|---|---|
| Component (mass %) |  | 2 | 3 | 4 | 5 | 6 | 7 |
| (A) Laureth-6 Carboxylic acid | AKYPO RLM-45 CA | 1.8 | 1.8 | 1.8 | 1.8 | 1.8 | 1.8 |
| Laureth-4 Carboxylic acid | AKYPO LM-26C | 0.09 | 0.09 | 0.09 | 0.09 | 0.09 | 0.09 |
| Lauric Acid | Lunac L-98 | 3.8 | 3.8 | 3.8 | 3.8 | 3.8 | 3.8 |
| Myristic Acid | Lunac MY-98 | 0.85 | 0.85 | 0.85 | 0.85 | 0.85 | 0.85 |
| Palmitic Acid | Lunac P-95 | 0.26 | 0.26 | 0.26 | 0.26 | 0.26 | 0.26 |
| Sodium Cocoyl Glutamate | AMISOFT CS-22B |  |  |  |  |  |  |
| Sodium Polyoxyethylene Lauryl Sulfate | Emal 227-PH11K2 |  |  |  |  |  |  |
| Lauryl Hydroxysultaine | AMPHITOL 20HD | 0.92 | 0.92 | 0.92 | 0.92 | 0.92 | 0.92 |
| Potassium Hydroxide |  | 1.55 | 2.16 | 1.54 | 1.54 | 1.54 | 1.54 |
| (D) Propylene Glycol |  | 10 | 10 | 10 | 10 | 10 | 10 |
| (B) Acrylates Copolymer | Carbopol AQUA SF-1 POLYMER | 0.05 | 3.0 |  |  |  |  |
| Carbomer | Carbopol 981 |  |  |  |  |  |  |
| Carbomer | Carbopol ETD 2050 |  |  |  |  |  |  |
| Acrylates/C10-30 Alkyl Acrylate Crosspolymer | Carbopol ETD 2020 |  |  |  |  |  |  |
| Acrylates/C10-30 Alkyl Acrylate Crosspolymer | Carbopol Ultrez 20 |  |  |  |  |  |  |
| Acrylates/C10-30 Alkyl Acrylate Crosspolymer | PEMULEN TR-2 POLYMERIC EMULSIFIER |  |  |  |  |  | 0.5 |
| Acrylates Copolymer | Carbopol AQUA SF-3 POLYMER |  |  |  |  |  |  |
| Hydroxyethyl Cellulose | HEC Daicel SE850K |  |  | 0.37 |  |  |  |
| Hydroxypropyl Cellulose | HPC M |  |  |  | 1.27 |  |  |
| Hydroxypropyl Guar Hydroxypropyltrimonium Chloride | Jaguar C-162 |  |  |  |  | 0.5 |  |
| (C) Purified Water |  | Balance | Balance | Balance | Balance | Balance | Balance |
|  | Total | 100 | 100 | 100 | 100 | 100 | 100 |
|  | (A) Total | 6.8 | 6.8 | 6.8 | 6.8 | 6.8 | 6.8 |
|  | (B) Total | 0.05 | 3 | 0.37 | 1.27 | 0.5 | 0.5 |
|  | (A)/(B) | 136 | 2.27 | 18.4 | 5.35 | 13.6 | 13.6 |
|  | Viscosity (Type-B Viscometer, 30° C.) [mPa · s] | 5.1 | 1351 | 84.9 | 109.4 | 70.2 | 254.2 |
|  | pH (30° C., Stock Solution) | 9.3 | 8.7 | 8.9 | 9.1 | 9.1 | 8.9 |
|  | Ease of Pressing Pump | 5 | 1 | 1 | 2 | 1 | 1 |
|  | Pressure upon Pressing Pump (50 mm/s) [N] | 29 | 67 | 81 | 57 | 77 | 70 |
|  | Elasticity of Foam upon Dispensing | 2 | Impossible to dispense | 2 | 2 | 2 | 2 |
|  | Dense feeling of Foam | 1 | Impossible to dispense | 3 | 3 | 3 | 2 |
|  | Quickness of Rinsing | a | Impossible to dispense | b | b | d | b |

The invention claimed is:

1. A cleanser, comprising:

a non-aerosol foaming container and, a liquid cleansing agent filled in the non-aerosol foaming container, wherein the liquid cleansing agent comprises the following components (A), (B), (C), and (D):

(A) least one member selected from the group consisting of lauric acid, myristic acid, palmitic acid, laureth-6 carboxylic acid, laureth-4 carboxylic acid, sodium cocoyl glutamate, and sodium polyoxyethylene lauryl sulfate, (B) from 0.1 to 1.5 mass % of a water-soluble polymer comprising a repeating unit derived from acrylic acid and/or alkyl acrylate, wherein, in terms of a viscosity of a 1-mass % aqueous solution thereof, a ratio of viscosity $v2$ at a shear rate of $1.0 \times 10^{-2}$ $(s^{-1})$ to viscosity $v1$ at a shear rate of $1.0 \times 10^{-1}$ $(s^{-1})$ is $v2/v1 \geq 5$, (C) water, and (D) from 5 to 50 mass % of a polyol.

2. The cleanser according to claim 1, wherein a mass ratio of the component (A) to the component (B), (A)/(B), is from 1 to 100.

3. The cleanser according to claim 1, wherein the liquid cleansing agent comprises from 1 to 20 mass % of the component (A).

4. The cleanser according to claim 1, wherein the liquid cleansing agent comprises from 0.2 to 1.5 mass % of the component (B).

5. The cleanser according to claim 1, wherein the viscosity $v2$ at a shear rate of $1.0\times10^{-2}$ $(s^{-1})$ of a 1-mass % aqueous solution of the component (B) is 1 Pa·s or more.

6. The cleanser according to claim 1, wherein the component (D) is a dihydric or trihydric alcohol.

7. The cleanser according to claim 1, wherein the liquid cleansing agent further comprises an amphoteric surfactant.

8. The cleanser according to claim 1, wherein a viscosity at 30° C. of the liquid cleansing agent is from 5 to 1,000 mPa·s.

9. The cleanser according to claim 1, wherein the non-aerosol foaming container is a pump foamer or a squeeze foamer.

10. The cleanser according to claim 9, wherein the non-aerosol foaming container is a pump foamer equipped with a filter from 90 to 400 mesh in a dispensing passage.

11. A cleansing method, the method comprising dispensing a foam of a liquid cleansing agent in a non-aerosol foaming container from the container, wherein the liquid cleansing agent comprises the following components (A), (B), (C), and (D):
  (A) least one member selected from the group consisting of lauric acid, myristic acid, palmitic acid, laureth-6 carboxylic acid, laureth-4 carboxylic acid, sodium cocoyl glutamate, and sodium polyoxyethylene lauryl sulfate,
  (B) from 0.1 to 1.5 mass % of a water-soluble polymer comprising a repeating unit derived from acrylic acid and/or alkyl acrylate, wherein, in terms of a viscosity of a 1-mass % aqueous solution thereof, a ratio of viscosity $v2$ at a shear rate of $1.0\times10^{-2}$ $(s^{-1})$ to viscosity $v1$ at a shear rate of $1.0\times10^{-1}$ $(s^{-1})$ is $v2/v1 \geq 5$,
  (C) water, and
  (D) from 5 to 50 mass % of a polyol; and
  spreading the foam over a skin to wash the skin.

12. The cleansing method according to claim 11, wherein the foam is poured onto one's hands, and spread directly by hand over the skin to wash the skin.

* * * * *